United States Patent
Dee et al.

(10) Patent No.: US 8,092,361 B2
(45) Date of Patent: Jan. 10, 2012

(54) SPLIT SPIN CENTRIFUGATION OF TEST ELEMENTS

(75) Inventors: Michael L. Dee, Livonia, NY (US);
Donald J. Moran, Jr., Rochester, NY (US); Mark Sawczuk, Rochester, NY (US); William G. Atterbury, Columbus, OH (US); Michael L. Marshall, Powell, OH (US); Douglas E. Boyd, Dublin, OH (US)

(73) Assignee: Ortho-Clinical Diagnostics, Inc., Rochester, NY (US)

( * ) Notice: Subject to any disclaimer, the term of this patent is extended or adjusted under 35 U.S.C. 154(b) by 841 days.

(21) Appl. No.: 12/114,375

(22) Filed: May 2, 2008

(65) Prior Publication Data

US 2009/0275458 A1 Nov. 5, 2009

(51) Int. Cl.
*B01D 21/26* (2006.01)
(52) U.S. Cl. ............................................. 494/37; 494/10
(58) Field of Classification Search ............... 494/7, 10, 494/37
See application file for complete search history.

(56) References Cited

U.S. PATENT DOCUMENTS

| | | | |
|---|---|---|---|
| 4,305,721 A | 12/1981 | Bernstein | |
| 5,256,376 A | 10/1993 | Callan et al. | |
| 5,260,868 A | 11/1993 | Gupta et al. | |
| 5,552,064 A | 9/1996 | Chachowski et al. | |
| 5,650,068 A | 7/1997 | Chachowski et al. | |
| 5,665,558 A | 9/1997 | Frame et al. | |
| 5,737,728 A | 4/1998 | Sisley et al. | |
| 5,814,276 A | 9/1998 | Riggs | |
| 5,826,236 A | 10/1998 | Narimatsu et al. | |
| 5,865,718 A | 2/1999 | Chan | |
| 5,890,134 A | 3/1999 | Fox | |
| 6,326,155 B1 | 12/2001 | Maclennan et al. | |
| 6,490,566 B1 | 12/2002 | Schmidt | |
| 6,606,529 B1 | 8/2003 | Crowder, Jr. et al. | |
| 7,069,097 B1 | 6/2006 | Barto et al. | |
| 7,072,732 B2 | 7/2006 | Muramatsu et al. | |
| 7,127,310 B1 | 10/2006 | Barto et al. | |
| 7,151,973 B1 | 12/2006 | Moll | |
| 2003/0064872 A1 | 4/2003 | Worthington et al. | |

(Continued)

FOREIGN PATENT DOCUMENTS

| | | |
|---|---|---|
| EP | 0 285 076 A2 | 10/1988 |
| EP | 0 285 076 A3 | 10/1988 |
| EP | 1 952 890 A2 | 8/2008 |
| GB | 2 359 772 A | 9/2001 |
| WO | WO 2009/076392 A1 | 6/2009 |

OTHER PUBLICATIONS

International Search Report and Written Opinion for International PCT Patent Application No. PCT/US2009/042323; Aug. 3, 2009; 11 Pages.

*Primary Examiner* — Walter Griffin
*Assistant Examiner* — Timothy Cleveland
(74) *Attorney, Agent, or Firm* — Hiscock & Barclay, LLP

(57) ABSTRACT

High-throughput centrifugation of batches of samples is achieved by dividing a single centrifugation run of a batch of samples into two or more staggered, discrete spins with fewer samples and in which the availability of centrifuge slots for loading or unloading of samples and the subsequent delivery of experimental results can be enhanced. The methodology is particularly useful in situations where multiple samples need to be processed rapidly, for example, as part of a STAT blood typing program in urgent care facilities prior to blood transfusion.

15 Claims, 5 Drawing Sheets

U.S. PATENT DOCUMENTS

| | | |
|---|---|---|
| 2004/0074825 A1 | 4/2004 | Schneider et al. |
| 2004/0166551 A1 | 8/2004 | Moulds et al. |
| 2005/0004828 A1 | 1/2005 | deSilva et al. |
| 2011/0003674 A1* | 1/2011 | Fox et al. .................. 494/7 |

* cited by examiner

SPLIT SPIN CENTRIFUGATION OF TEST ELEMENTS

FIELD OF THE APPLICATION

The application relates to an apparatus and a method for the high-throughput centrifugation of test samples.

BACKGROUND

The technique of column agglutination technology (CAT) employs an inert matrix and reagents for agglutination with filtration of formed agglutinates by centrifugation providing a visually indicative means for determining whether a reaction has occurred and if so, the grade of the reaction. First invented in the 1980s by LaPierre and associates, tests using CAT technology are now widely used in health care institutions for the rapid and reliable testing of blood samples. Typically, CAT tests comprise an immunodiagnostic test element such as a "bead cassette" or "gel card" with a number of microtubes, each containing a mixture of gel particles of dextran acrylamide and suitable reagents for performing an agglutination-type assay. For example, in the direct Coomb's assay, a patient's red cell suspension is first added to each microtube and after appropriate incubation with anti-human globulin serum (Coomb's reagent), the card is centrifuged. The results of the assay can then be simply 'read' from the card.

In recent years, CAT has been streamlined with the introduction of comprehensive platforms that use a variety of different types of sample receptacle that permit visible agglutination reactions to be observed. For example, one such platform is the ID-Micro Typing System® (Ortho-Clinical Diagnostics, Inc.) which is commonly used for blood grouping, antibody screening, antibody identification, phenotyping, and crossmatching of blood. Because the ID-Micro Typing System Gel Test® requires fewer procedural steps, it is easier to perform and more cost effective than other serological methods. Reduced handling also translates into fewer operator-induced errors and a more objective interpretation of results.

Despite these improvements, a major bottleneck for processing gel cards or similar test elements on current immunohematology platforms such as the ID-Micro Typing System® remains the centrifuge, which is programmed to run continuously for each "batch" loaded onto the system, without interruption, until the batch spin has been completed.

Information relevant to attempts to address this problem can be found in U.S. Pat. Nos. 7,151,973; 7,127,310; 7,072,732; 7,069,097; 6,606,529; 6,490,566; 5,890,134; 5,865,718; 5,826,236; 5,737,728; 5,260,868 and U.S. Publication Nos. US 2005/0004828; US 2004/0074825 and US 2003/0064872. Each one of these references suffers, however, from one or more of the following disadvantages: the references fail to remedy the rate-limiting centrifugation step and also fail to describe a procedure that could improve the overall efficiency of batch centrifugation.

For the foregoing reasons, there is an unmet need in the art to improve the throughput of batch centrifugation protocols.

SUMMARY OF THE APPLICATION

A method is described for performing the high-throughput centrifugation of a batch of samples. The invention further pertains to a testing apparatus and protocol for the automated operation of high-throughput centrifugation of batches of samples.

According to one aspect, a method is described for performing the centrifugation of batches of one or more sample receptacles, the method comprising (a) providing one or more primary batches, each comprising one or more sample receptacles, wherein each primary batch requires centrifugation for t number of seconds in a primary centrifuge, b) providing one or more secondary batches, each comprising one or more sample receptacles, (c) centrifuging the primary batches in one or more secondary centrifuges, (d) randomly pausing the operation of the secondary centrifuges N number of times, (e) loading or unloading each secondary centrifuge with one or more secondary batches, (f) resuming the centrifugation of the paused secondary centrifuges, wherein the frequency of unloading and reloading of the secondary centrifuges with the secondary batches is increased N fold as compared to the frequency of unloading and reloading of the primary centrifuge with each primary batch of sample receptacles.

The sample receptacles used according to this method can be any immunodiagnostic test element that is capable of producing a visible agglutination reaction that is accelerated by centrifugation.

The sample receptacles can contain patient samples, human blood samples or emergency samples, wherein reagents can further contain reagents for agglutination assays or blood typing.

According to the herein described method, there can be from 2 to 10 secondary centrifuges. The operation of the secondary centrifuges can be interrupted for unloading and reloading from 2 to 10 times.

In yet another aspect, the centrifuging, loading and reloading steps are each controlled by a control mechanism.

In yet another aspect, each secondary batch has the same number of sample receptacles.

In yet another aspect, the sample receptacles in each secondary batches are assessed for a result at the time of loading or reloading.

In yet another aspect, the centrifugation time of each secondary batch can be different from the centrifugation time of each of the other secondary batches.

In yet another aspect, the sample receptacles in each secondary batch are assessed for a result each time the centrifuge run is paused for loading or unloading.

According to another aspect, a method is described for performing the centrifugation of a batch of two or more sample receptacles, the method comprising the steps of (a) providing a primary batch of two or more sample receptacles, the primary batch requiring centrifugation for t number of seconds in a primary centrifuge, (b) dividing the primary batch into x number of secondary batches, (c) loading each secondary batch into each of y number of secondary centrifuges, (d) centrifuging each secondary batch for $t/x$ number of seconds, wherein the operation of each secondary centrifuge is staggered by at least $t/xy$ seconds, and (e) unloading and reloading each secondary centrifuge at least every $t/xy$ seconds, wherein the frequency of unloading and reloading of the secondary centrifuges with the secondary batches is increased by up to $xy$ fold as in comparison to the frequency of unloading and reloading of the primary centrifuge with the primary batch of sample receptacles.

According to one aspect, the unloading and loading occurs every $t/xz+z$ seconds, wherein z equals the number of seconds required for the loading and unloading. In one version, for example, z equals from 1 to 120 seconds.

The sample receptacles used according to this method can be any immunodiagnostic test element that is capable of producing a visible agglutination reaction that is accelerated by centrifugation.

The sample receptacles can contain patient samples, human blood samples or emergency samples, wherein reagents can further contain reagents for agglutination assays or blood typing.

According to the herein described method, there can be from 2 to 10 secondary centrifuges. There can also be from 2 to 10 secondary batches.

In yet another aspect, the dividing, centrifuging and reloading steps are each controlled by a control mechanism.

In yet another aspect, each secondary batch has the same number of sample receptacles.

In yet another aspect, every sample receptacle in each secondary batch is assessed for a result after centrifuging of each secondary batch for t/x number of seconds.

According to yet another version, a testing apparatus is provided that comprises (a) a plurality of centrifuges configured for the centrifugation of plurality of sample receptacles, (b) one or more drive mechanisms connected to the centrifuges, (c) at least one transfer mechanism configured for the loading or unloading of sample receptacles with respect to the centrifuges, and (d) a control mechanism interfaced with the drive mechanisms and the transfer mechanisms, which is configured for the operation of the centrifuges. The operation comprises the steps of the method comprising (i) providing one or more primary batches, each comprising one or more sample receptacles, wherein each primary batch requires centrifugation for t number of seconds in a primary centrifuge, (ii) providing one or more secondary batches, each comprising one or more sample receptacles, (iii) centrifuging the primary batches in one or more secondary centrifuges, (iv) randomly pausing the operation of the secondary centrifuges N number of times, (v) loading or unloading each secondary centrifuge with one or more secondary batches, (vi) resuming the centrifugation of the paused secondary centrifuges, wherein the frequency of unloading and reloading of the secondary centrifuges with the secondary batches is increased N fold as compared to the frequency of unloading and reloading of the primary centrifuge with said primary batch of sample receptacles.

In one embodiment, the testing apparatus includes a detector that is configured for the detection of agglutination reactions within the sample receptacles. The receptacles, in one version, are gel cards, bead cassettes or any other test element capable of producing a visibly detectable agglutination reaction. Preferably, the sample receptacles can be labeled with a bar code such that a bar code reader can read the receptacles, the apparatus further including an incubator for modulating the temperature of one or more samples.

The sample receptacles can contain human samples, human blood samples or emergency samples.

The sample receptacles can contain reagents for agglutination assays or blood typing.

There can be from 2 to 10 secondary centrifuges. There are can also be from 2 to 10 secondary batches. The centrifugation can be paused N number of times equal to 2 to 10.

In yet another embodiment, the testing apparatus is configured to assess every sample receptacle in each secondary batch for a result each time the centrifuge run is paused for loading or unloading.

According to yet another version, a testing apparatus is provided that comprises (a) a plurality of centrifuges configured for the centrifugation of plurality of sample receptacles, (b) one or more drive mechanisms connected to the centrifuges, (c) at least one transfer mechanism configured for the loading or unloading of sample receptacles with respect to the centrifuges, and (d) a control mechanism interfaced with the drive mechanisms and the transfer mechanisms, which is configured for the staggered operation of the centrifuges. The staggered operation comprises the steps of (i) providing a primary batch of two or more sample receptacles requiring centrifugation for t number of seconds in a primary centrifuge, (ii) dividing the primary batch into x number of secondary batches, (iii) loading each of the secondary batches into each of y number of secondary centrifuges, (iv) centrifuging each secondary batch for t/x number of seconds, wherein the operation of each of the secondary centrifuges is staggered by at least t/xy seconds, and (v) the unloading and reloading each of the secondary centrifuges occurs at least every t/xy seconds, wherein the frequency of the unloading and reloading of the secondary centrifuges with the secondary batches is increased by up to xy fold as in comparison to the frequency of unloading and reloading of the primary centrifuge with the primary batch of sample receptacles.

In one embodiment, the testing apparatus includes a detector that is configured for the detection of agglutination reactions within the sample receptacles. The receptacles, in one version, are gel cards, bead cassettes or any other test element capable of producing a visibly detectable agglutination reaction. Preferably, the sample receptacles can be labeled with a bar code such that a bar code reader can read the receptacles, the apparatus further including an incubator for modulating the temperature of one or more samples.

The unloading and loading of the sample receptacles can occur every $t/xz+z$ seconds, wherein z equals the number of seconds required for the loading and unloading. In one version, z can equal from 1 to 120 seconds.

The sample receptacles can contain human samples, human blood samples or emergency samples.

The sample receptacles can contain reagents for agglutination assays or blood typing.

There can be from 2 to 10 secondary centrifuges. There are can also be from 2 to 10 secondary batches. A secondary batch can contain from 2 to 100 sample receptacles.

In yet another embodiment, the frequency of reloading of the secondary centrifuges with the secondary batches is increased from 2 to 40 fold as in comparison to the frequency of reloading of the primary centrifuge with the primary batch of sample receptacles.

In yet another embodiment, the testing apparatus is configured for the rapid processing of one or more emergency samples.

In yet another embodiment, the testing apparatus is configured to assess every sample receptacle in each secondary batch for a result after centrifuging of each secondary batch for t/x number of seconds.

The previously described embodiments have many advantages, including the ability to increase the throughput of batch centrifugation, a reduction in time to result when samples are presented in smaller numbers than full batch quantities, a reduction in time to result when samples are not presented at the same time as well as a reduction in time to result and increased throughput for samples that can be clearly identified as not agglutinated after any one given discrete spin.

The methods disclosed herein are therefore particularly useful for the automation of high-throughput processing of test elements, especially as part of a STAT lane in an urgent care facility.

It should be understood that this application is not limited to the embodiments disclosed in this Summary, and it is intended to cover modifications and variations that are within the scope of those of sufficient skill in the field, and as defined by the claims.

DETAILED DESCRIPTION

Definitions

Figure 1:
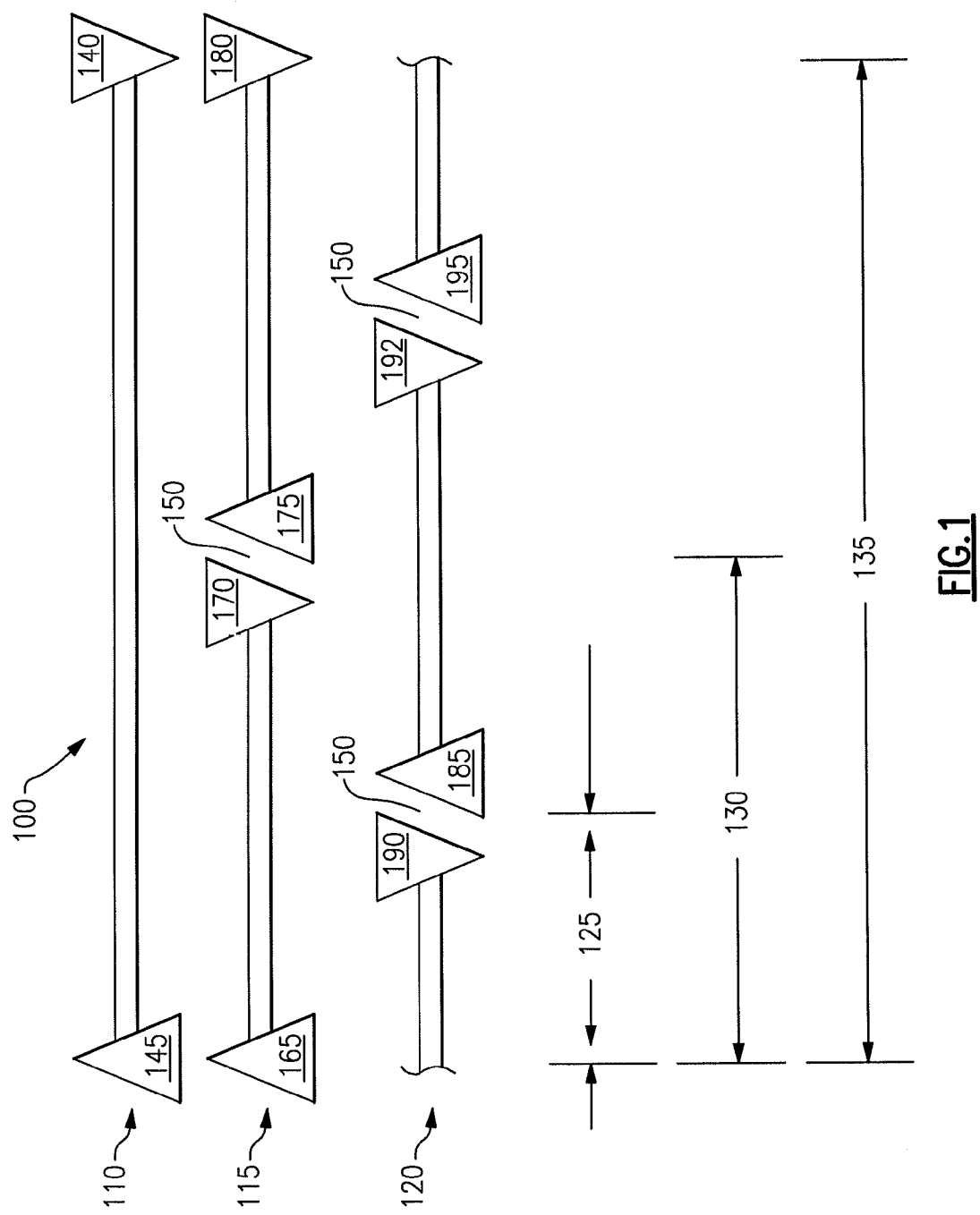
FIG. 1 illustrates a protocol for the high-throughput centrifugation of batches of samples in accordance with a first embodiment.

Unless defined otherwise, all technical and scientific terms used herein have the same meaning as is commonly understood by one of skill in the art. The following definitions are provided to help interpret the disclosure and claims of this application. In the event a definition in this section is not consistent with definitions elsewhere, the definition set forth in this section will control.

The term "plurality", as used herein, refers to a quantity of two or more.

As used herein, "batch" refers to a group of two or more entities, for example, two or more sample receptacles or samples.

"Agglutination", as used herein, refers to the clumping of a suspension of cellular or particulate antigen by a reagent, usually an antibody or other ligand-binding entity (see, for example, U.S. Pat. Nos. 4,305,721, 5,650,068 and 5,552,064, the contents of which are hereby incorporated herein by reference in their entirety). In another embodiment, the term "agglutination" refers to hemagglutination i.e. the agglutination of red blood cells. Hemagglutination can be used to identify red blood cell surface antigens (with known antibodies) or to screen for antibodies (with red blood cells expressing known surface antigens).

The term "particle", as used herein, may be any particle used in agglutination assays to which a ligand or ligand-binding molecule may be coupled. Particles may be cells, for example, bacteria or red blood cells or white blood cells or inert, microscopic solids made out of, for example, latex, although other types of particles to which a ligand may be coupled are also included within the scope of the invention. These inert particles may be comprised of any suitable material, such as glass or ceramics, carbon or plastic and/or one or more polymers, such as, for example, nylon, polytetrafluoroethylene (TEFLON™) or styrene-divinylbenzene polymers, or gel such as dextran acrylamide or sepharose. The particle size may be from about 0.1 micron to 1000 microns. Preferably, the particle size is from about 1 to about 10 microns.

As used herein, a "ligand" is any molecule which is capable of binding to a ligand-binding molecule. In another preferred embodiment, the ligand is exposed on the surface of an analyte as defined herein. In one embodiment, the ligand is an epitope of an antibody. For example, the ligand may be a component of a virus, bacteria or parasite. A ligand may be a surface antigen on a cell such as a red blood cell. A number of ligands are also known that bind immunoglobulin molecules and may be covalently coupled to the particles used in this application, for example Protein A, Protein G, Protein A/G and KappaLock™ (see also U.S. Pat. No. 5,665,558, the contents of which are herein incorporated by reference in its entirety). The ligand may bind to the isotype of the antibody which is used or tested for or, alternatively, one may use a bridging antibody, e.g., an IgG anti-IgM, for an IgM antibody. Thus, an IgG anti-IgM antibody would be coupled to the ligand as a "bridge" and an IgM antibody would bind to the IgG anti-IgM antibody.

The term "ligand-binding", as used herein, refers to a member of a binding pair, i.e., two different molecules wherein one of the molecules specifically binds to the second molecule through chemical or physical means. In addition to antigen and antibody binding pair members, other binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), and the like. Furthermore, binding pairs can include members that are analogs of the original binding member, for example, an analyte-analog or a binding member made by recombinant techniques or molecular engineering. If the binding member is an immunoreactant it can be, for example, a monoclonal or polyclonal antibody, a recombinant protein or recombinant antibody, a chimeric antibody, a mixture(s) or fragment(s) of the foregoing, as well as a preparation of such antibodies, peptides and nucleotides for which suitability for use as binding members is well known to those skilled in the art. A ligand-binding member may be a polypeptide affinity ligand (see, for example, U.S. Pat. No. 6,326,155, the contents of which are hereby incorporated by reference herein in its entirety). In one embodiment, the ligand-binding member is labeled. The label may be selected from a fluorescent label, a chemiluminescent label or a bioluminescent label, an enzyme-antibody construct or other similar suitable labels known in the art.

As used herein, the term "sample" refers to a material suspected of containing at least one analyte. The sample can be used directly as obtained from the source or following a pretreatment to modify the character of the sample. The sample can be derived from any biological source, such as a physiological fluid, including, blood, saliva, ocular lens fluid, cerebral spinal fluid, sweat, urine, milk, ascites fluid, raucous, synovial fluid, peritoneal fluid, amniotic fluid or the like. The sample can be pretreated before use, such as preparing plasma from blood, diluting viscous fluids, or the like; methods of treatment can involve filtration, distillation, concentration, inactivation of interfering components, and the addition of reagents. Besides physiological fluids, other liquid samples can be used. In addition, a solid material suspected of containing an analyte can be used as the sample. In some instances it may be beneficial to modify a solid sample to form a liquid medium or to release the analyte.

The term "analyte", as used herein, refers to the compound or composition to be detected or measured and which has at least one epitope or binding site or ligand. The analyte can be any substance for which there exists a naturally occurring binding member or for which a binding member can be prepared. Analytes include, but are not limited to, toxins, organic compounds, proteins, peptides, microorganisms (bacteria, viruses or parasites and the like), amino acids, nucleic acids, hormones, steroids, vitamins, drugs, virus particles and metabolites of or antibodies to any of the above substances. The term "analyte" also includes any antigenic substances, haptens, antibodies, macromolecules and combinations thereof. In one embodiment, the analyte is a cell surface antigen. In another embodiment, the analyte is a surface antigen of a red blood cell.

As used herein "blood" broadly includes whole blood or any component of whole blood, such as red blood cells, plasma or serum.

As used herein, "red blood cells" (RBCs) used in the application may be isolated from whole blood by centrifugation or through a density gradient such as a Ficoll gradient.

As used herein, "centrifugation" refers to the rotation of an object about an axis of rotation.

As used herein, a "test element" or "immunodiagnostic test element" refers to any receptacle for performing a particle agglutination reaction that requires a centrifugation step. In one embodiment, a test element is a bead cassette or gel card. Preferably, the degree of particle agglutination within a test element can be determined using a detector or visually.

As used herein, "bead cassette" refers to an assembly of one or more containers, typically on a card, that are filled with beads for performing an agglutination assay that requires a centrifugation step. In one embodiment, the cassette comprises one or more microtubes.

As used herein, a "gel card" refers to a test element with two or more microtubes. In one embodiment, the gel card is an ID-Micro Typing System® gel card. Such cards measure approximately 2.0×2.75 inches and typically contain up to 6 microtubes, each pre-filled with a gel for agglutinating red blood cells present in a sample. Further description can be found in U.S. Pat. Nos. 5,650,068 and 5,552,064, both of which are hereby incorporated herein by reference in their entirety.

As used herein, the term "bead" refers to a discrete solid that may be spherical (e.g., microspheres) or have an irregular shape. Beads may be as small as approximately 0.1 µm in diameter or as large as approximately several millimeters in diameter. Beads may comprise a variety of materials including, but not limited to ceramic, plastic, glass, polystyrene, methylstyrene, acrylic polymers, dextran acrylamide, sepharose, cellulose and the like.

As used herein, the term "staggered" refers to the operation of two or more centrifuges, where the centrifugation cycle of one centrifuge overlaps with a part of the centrifugation cycle of each of the other centrifuges.

As used herein, the numbers "x", "y", "z" and "t", refer to whole integers.

The term "frequency", as used herein, refers to how often a centrifuge becomes available for loading or unloading of sample receptacles.

The term "sample receptacle", as used herein, refers to any container that can be centrifuged. For example, a sample receptacle can be a tube, a microtiter plate, a column or a bead cassette. The sample receptacle can be made of plastic or glass or any other material that can be centrifuged without deforming its shape. In another embodiment, the sample receptacle is made of an inert material that does not promote the adhesion of a biological sample to the internal walls of the sample receptacle. In an exemplary embodiment, the sample receptacle is made out of acrylic or polypropylene. In yet another exemplary embodiment, the sample receptacle is a gel card or bead cassette containing one or more microtubes. In yet another embodiment, the walls of the sample receptacle are transparent and can transmit electromagnetic radiation of a wavelength from 200 nm to 700 nm.

As used herein, "detector" refers to an apparatus for the detection of particle agglutination, typically a photodetector (see, for example, U.S. Pat. No. 5,256,376 and published U.S. patent application US 2004/0166551, the contents of which are hereby incorporated herein by reference in their entirety). In one embodiment, the apparatus can detect bioluminescence or chemiluminescence or fluorescence. In another embodiment, the detector is an imager.

As used herein, a "control mechanism" refers to one or more computers and the associated hardware and software that monitor and control various aspects of the testing apparatus, including, but not limited to, one or more drive mechanisms, one or more detectors, one or more readers and one or more transfer mechanisms. In one aspect, the computer provides one or more hard drives or equivalent hardware for the encrypted storage of patient information. In another aspect, the computer is connected to the local area network (LAN) at the health care facility by standard wired or wireless networking capabilities. In another aspect, the computer provides software for the comprehensive analysis of the results and associates this information with the stored patient record and designated bar code. In yet another aspect, the "control mechanism" is provided by a stationary desktop computer or a notebook computer. The computer may be networked to a local printer.

As used herein, a "transfer mechanism" refers to any means of transporting sample receptacles within the apparatus and can include robotic arms, grippers, conveyor belts and the like for moving samples and sample receptacles from one location to another. For example, transfer mechanisms such as one or more robotic arms can move one or more sample receptacles from a bar code reader to one or more centrifuges or from one or more centrifuges to one or more detectors.

As used herein, an "incubator" is an apparatus that increases or decreases the temperature of a sample. In one embodiment, the incubator heats a sample to 37 degrees Celsius.

As used herein, "STAT" is a medical term derived from the Latin word "statim" which means immediately. A "STAT lane" therefore refers to the urgent or rush processing of patient samples.

As used herein, "emergency sample" refers to any sample that requires immediate processing. Emergency samples typically include those samples collected in emergency rooms or other urgent care facilities. For example, an emergency room sample can be a blood sample taken from a patient in an emergency room that needs to be typed rapidly before administering a blood transfusion to the patient.

As used herein, "reagents for particle agglutination" refer to any compound which is required for an agglutination reaction to occur. For example, reagents include, but are not limited to, buffers, ligands, ligand-binding molecules and associated particles as defined herein.

As used herein, "reagents for blood typing" refer to those reagents required blood typing such as the direct or indirect Coomb's test or equivalent assay for determining the blood group of a blood sample. For example, a reagent for blood typing can be Coomb's reagent i.e. a preparation of antibodies, raised in animals, directed against one of the following human immunoglobulin, complement or a specific immunoglobulin e.g. anti-human IgG for use in the Coomb's test.

As used herein, the term "antibody" includes both polyclonal and monoclonal antibodies; and may be an intact molecule, a fragment thereof (such as Fv, Fd, Fab, Fab' and F(ab)'2 fragments, or multimers or aggregates of intact molecules and/or fragments; and may occur in nature or be produced, e.g., by immunization, synthesis or genetic engineering. The antibody or antigen used herein is dependent upon the antibody or antigen that is being tested. For example, the number of blood group antigens and thus, antibodies to these antigens that have been identified is very large, with more antigens and antibodies continually being determined. The International Society of Blood Transfusion has published a non-exclusive list of red cell antigens in Blood Group Terminology 1990, Vox. Sang. 58:152-169 (1990 and includes, but is not limited to, antibodies and antigens A, B, D, C, c, Cw, E, e, K, Fya, Fyb, Jka, Jkb, S and s.

As used herein, "to assess a result" refers to the determination of either a positive or negative assay in each test element. In one embodiment, the test element, such as a bead cassette or gel card, contains one or more column agglutination type assays. For example, the presence of agglutination indicates a positive result whereas the absence of agglutination is interpreted as a negative result. In another embodiment, at the conclusion of each discrete spin, the test elements are photographed for analysis by image analysis software. If the computer can accurately determine the results, i.e. the presence or absence of agglutination, the results can be recorded and the test elements removed from the centrifuge thereby increasing the overall throughput of the instrument.

The following description relates to certain preferred embodiments of the application, and to a particular methodology for the batch centrifugation of test elements. As will be readily apparent from the discussion, the inventive concepts described herein are broadly applicable to any centrifugation procedure where large batches of samples need to be processed with maximum throughput.

In one embodiment, the centrifugation protocol described herein is used to process particle agglutination type assays within a workstation such as the AutoVue® (Ortho-Clinical Diagnostics, Inc.) or similar platforms for blood analysis. Blood analysis platforms typically use either a gel card or a bead cassette. In the instance of gel cards, this test element includes microtubes that are pre-dispensed with a mixture of gel particles and reagents for particle agglutination, such as anti-human globulin (Coomb's reagent) serum and diluent. A measured amount of the desired red cell suspension from a patient, typically a few microliters, is added first to each microtube within a gel card and incubated at 37° C. for a predetermined time, typically a few minutes, before being centrifuged. After centrifugation. the test results are read and graded according to the degree of agglutination. If agglutination occurs, red cell agglutinates are trapped in the gel suspension during centrifugation. Large agglutinates are immobilized toward the top of the gel column, whereas smaller agglutinates are trapped lower in the gel column. Red cells with no bound antibody are forced through the gel particles during centrifugation and settle as a pellet in the microtube tip at the bottom of the tube. A major advantage of the procedure is that it obviates the need for cell washing. Appropriate positive and negative controls may also be added as needed. As mentioned previously, the centrifugation step is rate-limiting in that the loading and unloading of samples can only occur once the centrifugation run is completed.

The novel split-spin centrifugation protocol, described in this application, proposes a regimen that increases the availability of centrifuges and reduces the time from loading to result analysis.

Referring to FIG. 1, the diagram 100 depicts a series of centrifugation protocols and the time required for each centrifugation step. The single, uninterrupted centrifugation protocol 110 of, for example, 24 test elements that are disposed within a single dedicated centrifuge is depicted along a time scale starting at time 145 and completing the cycle at time 140, as shown by block 135, 10 minutes later. According to this standard protocol 110, the centrifuge only becomes available for loading and unloading every 10 minutes i.e. at the conclusion of the cycle.

In accordance with a first embodiment, split centrifugation protocols 115 and 120 are provided in which the batch of 24 test elements of FIG. 1 is divided into two (2) smaller batches of 12 cards each. The smaller batches of 12 test elements are centrifuged in two separate centrifuges that operate for half as long as protocol 110 (i.e., 5 minutes), as shown by arrow 130, and in a staggered configuration with respect to each other.

More specifically and for the first centrifuge, the cycle 115 starts at time 165 and stops five minutes later at time 170. After a period 150 for loading and reloading of additional test elements, a second cycle initiates with the first centrifuge starting at time 175 and stopping 5 minutes later at time 180.

In the meantime and per the staggered protocol 120 for the second centrifuge, the cycle starts at time 185 and finishes 5 minutes later at time 192, which is 2.5 minutes later than time 175 of the first centrifuge. After another period 150 for loading and reloading of additional test elements, a second cycle commences at time 195 and proceeds for another 5 minutes terminating 2.5 minutes later than time 180.

By staggering the operation of the first and second centrifuges by, in this example, 2.5 minutes, as shown in 125, it becomes apparent that the availability of centrifuge slots is significantly increased because a centrifuge becomes available for loading or unloading every 2.5 minutes i.e. at times 190, 170, 192 and 180 instead of every 10 minutes as depicted in the standard protocol 110. FIG. 1 therefore illustrates how, by dividing a batch of samples by two and providing two centrifuges, the frequency of unloading/loading of a centrifuge is increased up to four fold depending on the time 150 which is taken to load and/or reload either centrifuge.

A person of ordinary skill in the art will recognize that the described embodiment can be altered in a number of ways and still fall within the intended scope of the application and the initial batch of samples can be divided into any pre-determined number of multiple smaller batches. For example, as described in exemplary fashion with regard to FIGS. 2-4, the method disclosed herein can be used with more than two centrifuges.

Figure 2:
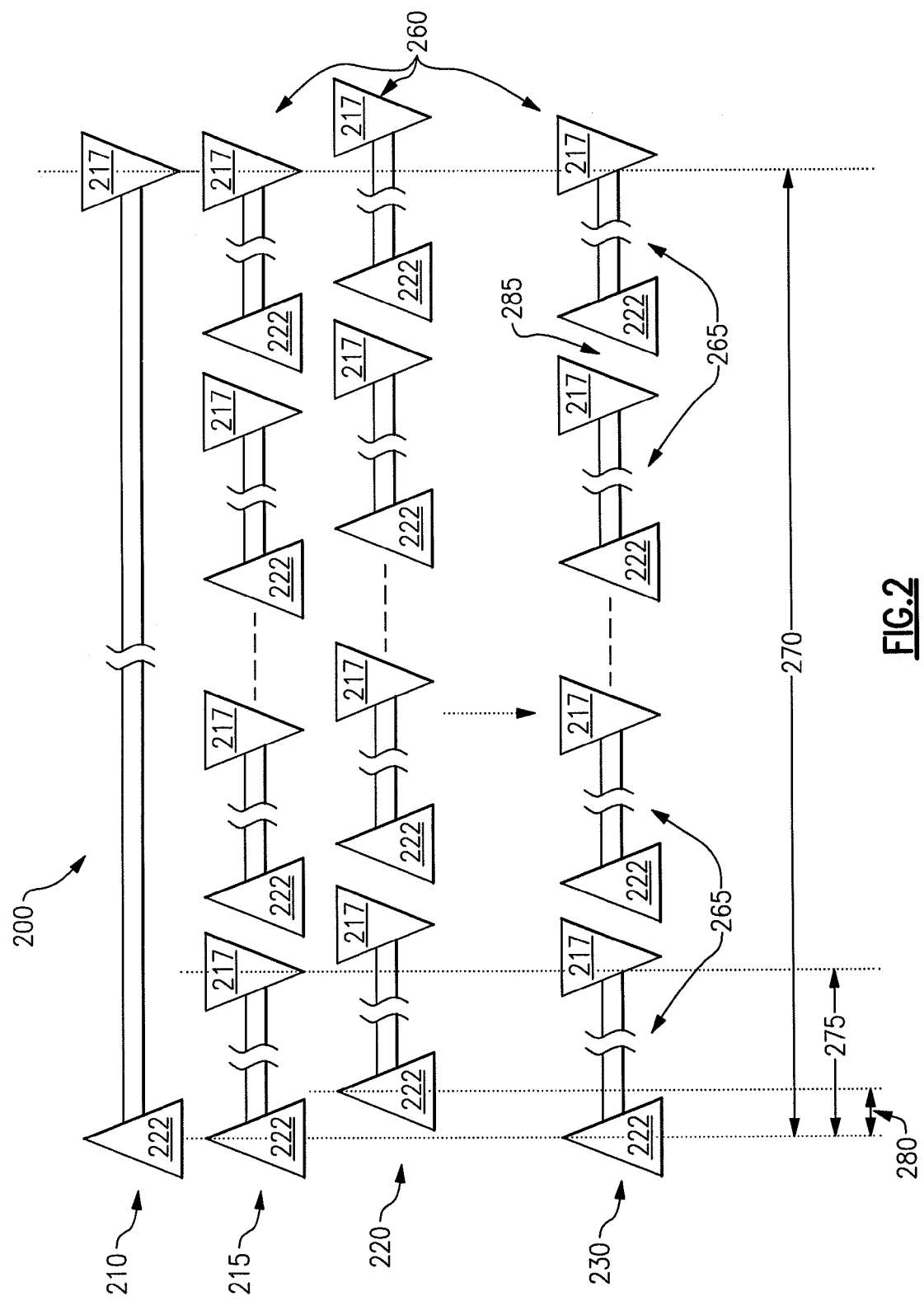
FIG. 2 illustrates a protocol for the high-throughput centrifugation of a plurality of batches of samples in accordance with a second embodiment.

First and referring to FIG. 2, diagram 200 depicts a split-spin centrifugation protocol using multiple centrifuges and multiple batches of samples. According to this example, cycle 210 represents the so-called standard centrifugation protocol for a single batch of samples needing centrifugation for a period of time 270 equal to t number of seconds. By dividing the original batch of samples into x number of minibatches, as depicted in FIG. 2 by the arrows 265, each minibatch can be loaded into y number of centrifuges, whose cycles are depicted by arrows 260, for a time period 275 equal to t/x seconds, corresponding to the time required for each centrifugation run starting at a time 222 and ending at a time 217. The time period 285 needed to load or unload each of the minibatches is equal to z seconds. By staggering the operation of each centrifuge by period 280, equal to t/xy seconds, as shown by cycles 215, 220 and 230, the frequency of loading and unloading of a centrifuge can be increased by up to xy fold as compared to the frequency of loading and unloading of a single centrifuge in cycle 210 containing the single original batch of samples and running for the period 270 equal to t number of seconds.

The split spin protocol described herein provides an opportunity to assess every sample receptacle for a result after each discrete spin of t/x seconds. Sample receptacles such as gel cards that are already identifiable as negative or positive can have the result recorded and removed from the centrifuge without the need to proceed with the remaining spin time of t−t/x seconds. This capability reduces time to result and frees up available slots within each of the centrifuges thereby further increasing the overall throughput of the split-spin centrifugation protocol.

A person of ordinary skill in the art will recognize that the described centrifugation protocol may be modified to include a random split spin protocol in which the centrifugation of a batch of test elements may be randomly 'split' into potentially any number of smaller centrifugation spins of variable duration.

Figure 5:
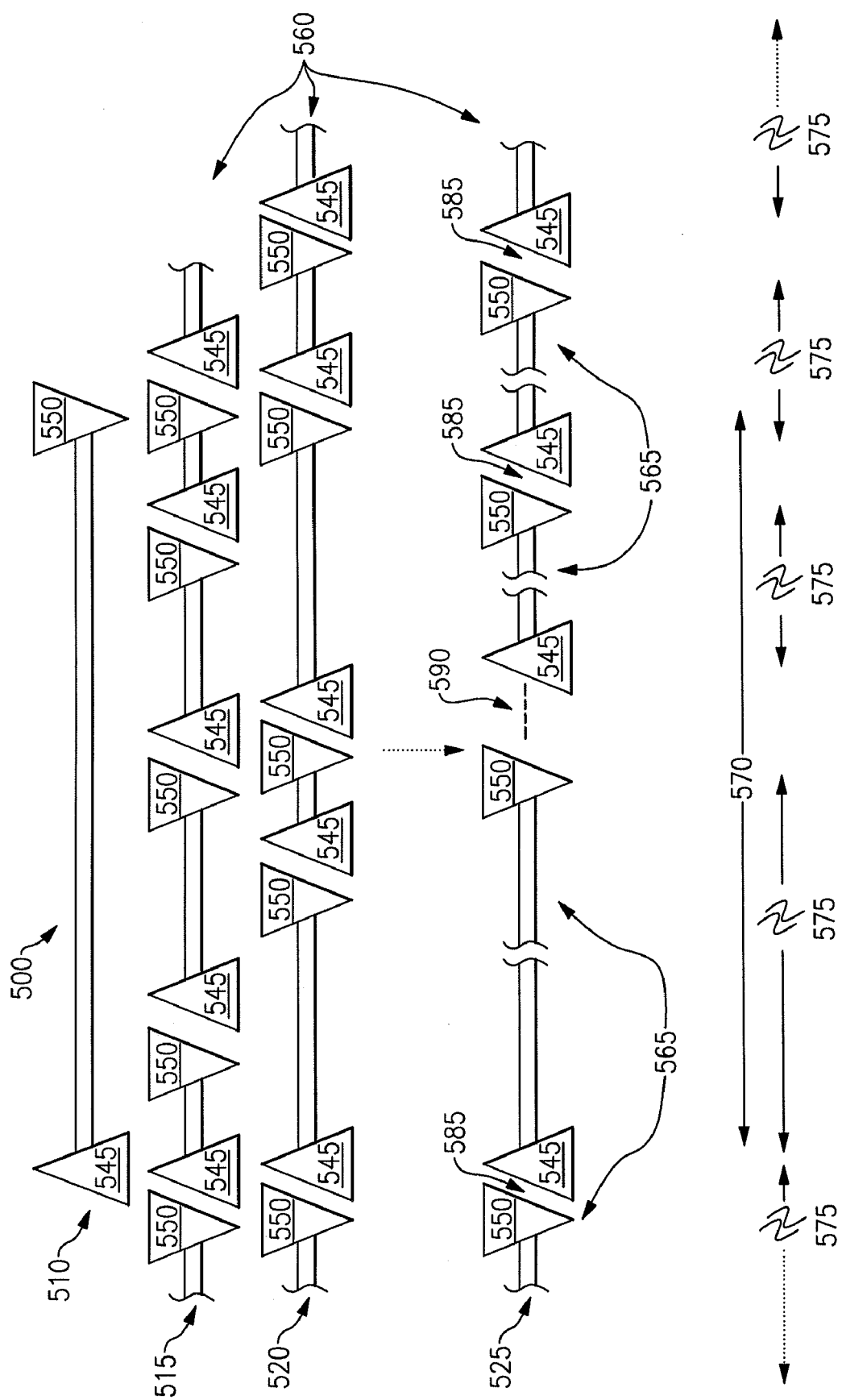
FIG. 5 illustrates a protocol for the high-throughput centrifugation of a plurality of batches of samples in accordance with a fourth embodiment.

Referring to FIG. 5, diagram 500 depicts a random split-spin centrifugation protocol using multiple centrifuges and multiple batches of samples. Cycle 510 represents a standard centrifugation protocol in which one or more batches of test elements are centrifuged for a time period 570. According to a random split spin centrifugation protocol, one or more primary batches of test elements are first distributed amongst one or more centrifuges as depicted in 560. As soon as centrifugation starts, the centrifuges are randomly selected to pause for a time period 585 thus permitting the loading or unloading of test elements according to whether or not the test elements have completed the pre-determined centrifugation time allotted to that particular sample. For example, in protocol 515, the centrifuge is shown to start at 545 and stop at 550 i.e. 4 times within the time period 570. In another example, protocol 520, a second centrifuge stops at 545 and starts at 550 for a total of 3 times during the time period 570.

A person of ordinary skill will again recognize that the random split spin protocol permits a centrifugation spin to be randomly paused for unloading or reloading of test elements, thereby increasing the throughput of centrifugation. For example, the centrifugation of one or more primary batches of test elements may be randomly selected to pause for a time period 585. According to this scenario, depicted in protocol 525, a centrifugation time period 570 is randomly split into any number 590 of discrete spins 565 of variable duration 575. Hence, the frequency of loading and unloading of a centrifuge having a random split spin centrifugation protocol can be increased as compared to the frequency of loading and unloading of a single centrifuge in cycle 510 containing a single batch of samples and running for the time period 570. The number of breaks in a random split spin centrifugation protocol may be only limited by the time desired to result.

In another embodiment, each test element is assessed for a result after each discrete spin i.e. in this example, at time points 550. Test elements that are determined to be either negative or positive can have the result recorded and removed from the centrifuge without the need to proceed with the remaining spin time. This capability further reduces time to result and frees up available slots within each of the centrifuges thereby further increasing the overall throughput.

Figure 3:
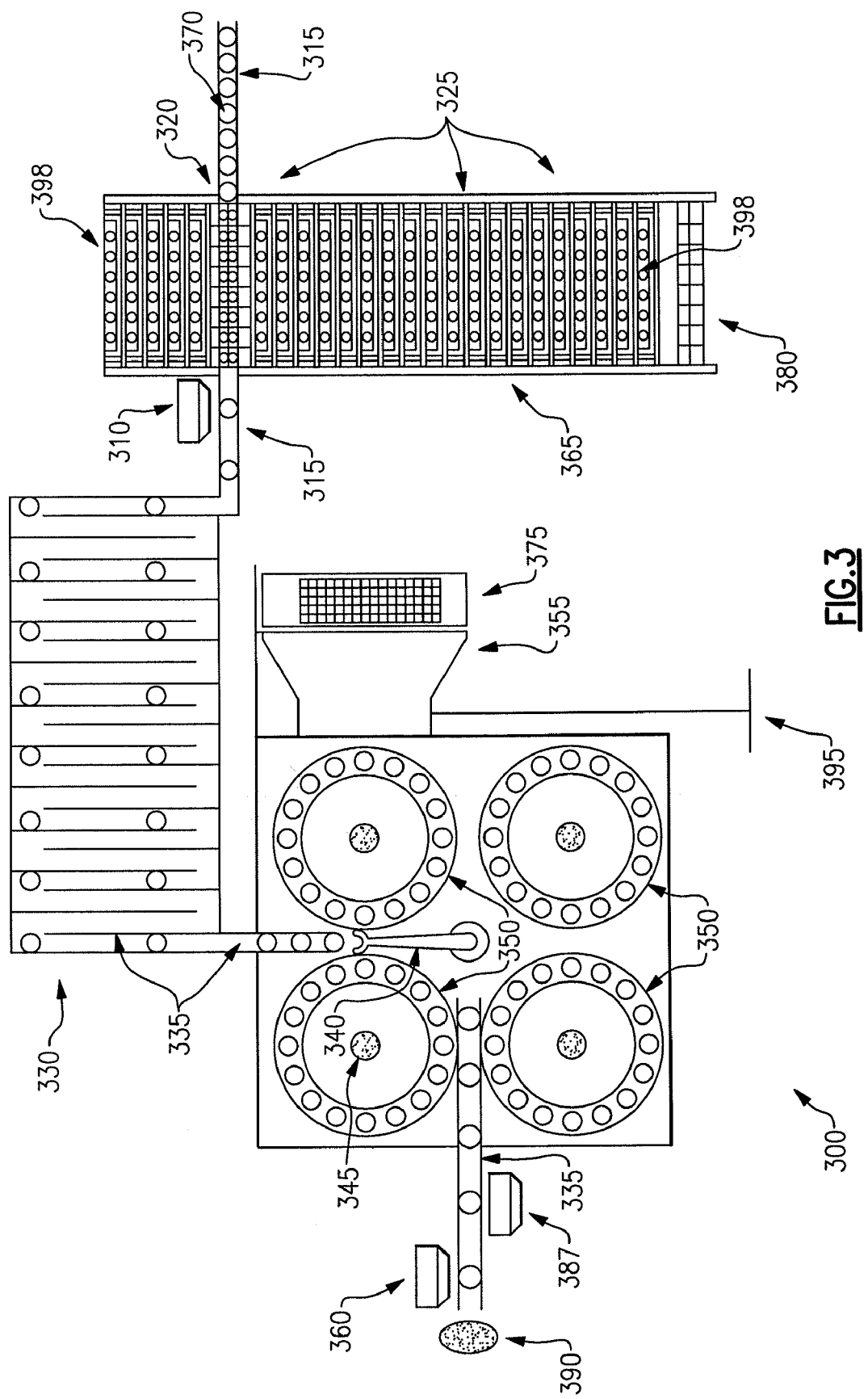
FIG. 3 depicts a plan view of a workstation that is capable of employing a high throughput centrifugation protocol.

For purposes of employing a protocol for centrifugation as described herein, an exemplary apparatus is provided. More specifically, a blood typing workstation for split-spin centrifugation is described. Referring to FIG. 3, the workstation 300 includes a dedicated computer 355 with appropriate software for the storage and analysis of experimental results without human intervention. The computer means of the workstation 300 preferably includes a microprocessor, a keyboard 375 or other input device for programming the microprocessor, memory and data storage as well as networking means 395. Feedback is provided to provide the microprocessor with position information of contained patient receptacles and equipment in the workstation 300 on a continual basis. Patient records and test results can be monitored remotely in real time. An exemplary description of a blood sample processing systems is taught in greater detail in U.S. Pat. No. 5,814,276, the contents of which are hereby incorporated herein in their entirety.

In operation, laboratory personnel load vials containing patient blood samples into empty sample racks 380 at a loading station 325. The racks 398 are then transported by means of a rack conveyor belt 365 to a pipetting station 320, where an aliquot of the blood samples is automatically aspirated from the sample vials and loaded into a test element, such as the herein described gel cards and/or bead cassettes, for hemagglutination. Each test element is preferably pre-labeled with a unique bar code that identifies element specific information including, but not limited to lot number, expiration date, date of manufacture and other pertinent information. A conveyor belt 315 transports the test elements 370 past a bar code reader 310. The computer 355 can then associate the bar code with a patient's record. The conveyor belt transports the test elements 370 through an incubator 330 which is maintained at a temperature of 37 degrees Celsius. The form of the incubator used is not necessarily critical provided it can accommodate test elements suitably. After travel through the incubator 330, a robotic arm 340 then loads the test elements into any one of four available centrifuges 350 that are disposed in adjacent relation to one another.

Figure 4:
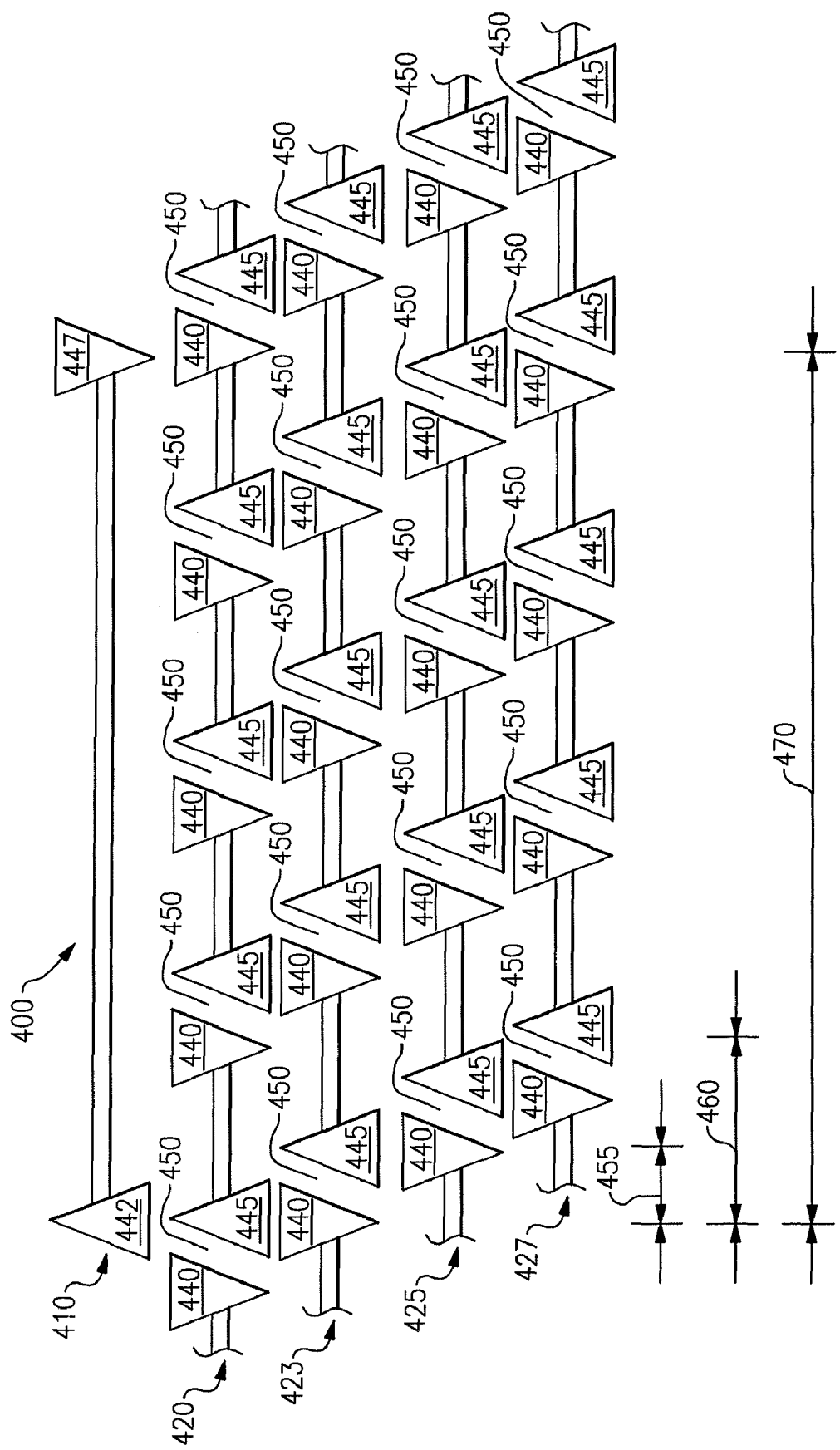
FIG. 4 illustrates a protocol for the high-throughput centrifugation of batches of samples in accordance with a third embodiment for use in the workstation of FIG. 3.

The stop-start schedule of the centrifuges and associated drive mechanisms 345 are controlled by the computer 355 according to a pre-programmed split spin centrifugation protocol 400, FIG. 4.

Referring to FIG. 4, reference numeral 410 again depicts, for comparison purposes, a standard protocol of a single centrifuge starting with, for example, 16 test elements that require centrifuging for 24 minutes. The cycle starts at time 442 and finishes 24 minutes later at time 447. By dividing the 16 test elements into 4 minibatches of four test elements each, each minibatch can therefore be centrifuged for the time period 460 equal to 24/4=6 minutes. If four centrifuges are used and the operation of each centrifuge is staggered with respect to each of the other centrifuges by a period 455, equal to 24/4×4=1.5 minutes, a centrifuge 350, FIG. 3, becomes available for loading or unloading every 1.5 minutes. Depending on the time period 450 needed for unloading and reloading of each centrifuge 350, the frequency of loading and reloading can be increased up to 4×4=16 fold as compared with the centrifugation of the 16 test elements in a single centrifuge for a 24 minute run.

In another embodiment, the stop-start schedule of the centrifuges and associated drive mechanisms 345 are controlled by the computer 355 according to a pre-programmed random split spin centrifugation protocol 500, FIG. 5 and discussed above. According to this scenario, the centrifugation of one or more batches of test elements lasting a time period equal to time period 570 is randomly split into potentially any number of discrete spins 565 of variable duration 575. The number of discrete spins is only limited by the desired time to result of a particular batch of test elements. The computer tracks each test element and determines when centrifugation of a particular test element is complete. The computer then coordinates the loading and unloading of the centrifuges at the end of each discrete spin thereby increasing overall throughput of the apparatus.

With this understanding of the staggered operation of each of the centrifuges 350 and referring again to FIG. 3, when one of the four centrifuges 350 stops, the computer 355 determines which test elements have completed the requisite 24 minute centrifugation period and directs the robotic arm 340 to remove the selected test elements from the centrifuge to the conveyor belt 335. The test elements then pass in front of a bar code reader 387 and detector 360 prior to disposal in the eject slot. Data from the bar code reader 387 and detectors 360 are processed and analyzed by the computer 355. The results of the hemagglutination test can then be displayed on a monitor or sent to centralized server via a local area network 395 (LAN), shown diagrammatically. In an alternative embodiment, a camera may be used to photograph each test element. Results of the agglutination test are then assessed by the computer 355 using image analysis software.

In another embodiment, each test element is photographed after each discrete spin i.e. in this example, every 6 minutes. Test elements that are determined by the computer to be either negative or positive can have the result recorded and removed from the centrifuge without the need to proceed with the remaining spin time, i.e., in this example, 24−6=18 minutes. This capability reduces time to result and frees up available slots within each of the centrifuges thereby further increasing the overall throughput of the instrument.

The split-spin centrifugation workstation 300 for blood typing as described above is fully automated, efficient and requires minimal human intervention. The apparatus is therefore ideally suited for STAT lanes at urgent care facilities where, for example, blood samples need to be processed rapidly in order to determine if a donor's blood is compatible with a patient's before blood transfusion.

PARTS LIST FOR FIG. 1-5

100 Centrifugation protocol
110 Standard centrifugation protocol
115 Stop-start protocol for first centrifuge
120 Stop-start protocol for second centrifuge
125 Stop-start period
130 Split spin period
135 Full Split spin period
140 Centrifuge stopping point, time
145 Centrifuge starting point, time
150 Loading/reloading point, time
165 Centrifuge starting point, time
170 Centrifuge stopping point, time
175 Centrifuge starting point, time
180 Centrifuge stopping point, time
185 Centrifuge starting point, time
190 Centrifuge stopping point, time
192 Centrifuge stopping point, time
195 Centrifuge starting point, time
200 Centrifugation protocol
210 Standard centrifugation protocol
215 Stop-start protocol for first centrifuge
217 Centrifuge stopping point, time
220 Stop-start protocol for second centrifuge
222 Centrifuge starting point, time
230 Stop-start protocol for centrifuge number y
260 y number of centrifuges
265 x number of minibatches
270 Full Split spin period
275 Split spin period
280 Stop-start period
285 Loading/reloading period
300 Workstation
310 Bar code reader
315 Conveyor belt
320 Pipetting station
325 Loading station
330 Incubator
335 Conveyor belt
340 Robotic arm
345 Drive Mechanism
350 Centrifuges
355 Computer
360 Detector
365 Rack conveyor belt
370 Test element
375 Keyboard
380 Sample rack
387 Bar code reader
390 Biohazard waste
395 Local area network
398 Sample racks
400 Centrifugation protocol
410 Standard centrifugation protocol
420 Stop-start protocol for first centrifuge
423 Stop-start protocol for second centrifuge
425 Stop-start protocol for third centrifuge
427 Stop-start protocol for fourth centrifuge
442 Centrifuge starting point, time
447 Centrifuge stopping point, time
450 Loading/reloading period
455 Stop-start period
460 Split spin period
470 Full Split spin period
500 Centrifugation protocol
510 Standard centrifugation protocol
515 Stop-start protocol for first centrifuge
520 Stop-start protocol for second centrifuge
525 Stop-start protocol for centrifuge number y
545 Centrifuge starting point, time
550 Centrifuge stopping point, time
560 y number of centrifuges
565 x number of secondary batches
570 Standard spin period
575 Random split spin period
585 Loading/reloading period
590 N number of random split spins While this invention has been particularly shown and described with references to preferred embodiments thereof, it will be understood by those skilled in the art that various changes in form and details may be made therein without departing from the intended scope of the invention encompassed by the following appended claims.

The invention claimed is:

1. A method of batch centrifugation of test samples, said method comprising the steps of:
    a) creating a plurality of smaller secondary batches from a primary batch of test samples, wherein said primary batch typically requires centrifugation for a time period equal to t in a primary centrifuge and the number of secondary batches is equal to y, which is at least 2;
    b) loading the test samples of said secondary batches into x number of separate secondary centrifuges, in which x is at least 2;
    c) staggering the operation of said x number of secondary centrifuges by a time period t/xy in relation to one another over a total centrifugation cycle for each secondary centrifuge that is equal to time period t;
    d) pausing the operation of each of said staggered secondary centrifuges;
    e) at least one of loading new test samples and unloading completed test samples from each of said paused secondary centrifuges during said pausing step; and f) resuming said centrifugation of said paused secondary centrifuges, wherein the frequency of said unloading and reloading of each of said secondary centrifuges with said secondary batches is increased xy fold as compared to the frequency of unloading and reloading of a primary centrifuge loaded with a primary batch of test samples.

2. The method of claim 1, wherein said test samples are disposed within sample receptacles.

3. The method of claim 2, wherein said sample receptacles are bead cassettes.

4. The method of claim 2, wherein said bead cassettes are gel cards.

5. The method of claim 2, wherein said sample receptacles contain human samples.

6. The method of claim 2, wherein said sample receptacles contain human blood samples.

7. The method of claim 2, wherein said sample receptacles contain only emergency samples.

8. The method of claim 2, wherein said sample receptacles comprise reagents for particle agglutination assays.

9. The method of claim 2, wherein said sample receptacles comprise reagents for blood typing.

10. The method of claim 1, wherein the number of secondary centrifuges is from 2 to 10.

11. The method of claim 1, wherein the steps of centrifuging, loading and reloading are controlled by a control mechanism.

12. The method of claim 1, wherein each of said secondary batches have the same number of test samples.

13. The method of claim 1, wherein said test samples in each of said secondary batches are assessed for a result at the time of loading or reloading.

14. The method of claim 1, wherein the centrifugation time of each of said secondary batches can be different from the centrifugation time of each of the other said secondary batches.

15. The method of claim 2, wherein sample receptacles in each of said secondary batches are assessed for a result at said pausing step.

* * * * *